(12) United States Patent
Navarro et al.

(10) Patent No.: US 7,635,354 B2
(45) Date of Patent: Dec. 22, 2009

(54) DEVICE FOR FIXING A CATHETER TO THE BODY OF A PATIENT

(76) Inventors: Francis Navarro, 26 Avenue de la Croix du Capitaine, Bâtiment F, 34000 Montpellier (FR); Jacques Le Bozec, La Grand Village, 35500 La Chapelle Erbree (FR)

( * ) Notice: Subject to any disclaimer, the term of this patent is extended or adjusted under 35 U.S.C. 154(b) by 0 days.

(21) Appl. No.: 10/549,312

(22) PCT Filed: Mar. 9, 2004

(86) PCT No.: PCT/FR2004/000560

§ 371 (c)(1),
(2), (4) Date: Aug. 31, 2006

(87) PCT Pub. No.: WO2004/087250

PCT Pub. Date: Oct. 14, 2004

(65) Prior Publication Data

US 2007/0043326 A1  Feb. 22, 2007

(30) Foreign Application Priority Data

Mar. 19, 2003 (FR) .................................. 03 03350

(51) Int. Cl.
*A61M 5/32* (2006.01)
(52) U.S. Cl. ................. 604/174; 604/175; 604/180
(58) Field of Classification Search ............ 604/93.01, 604/174–175, 177–178, 180, 263, 513, 539–541, 604/543; 128/DIG. 6, DIG. 26
See application file for complete search history.

(56) References Cited

U.S. PATENT DOCUMENTS

| 4,517,971 | A |  | 5/1985 | Sorbonne | |
| 4,659,329 | A | * | 4/1987 | Annis | 604/180 |
| 5,306,253 | A | * | 4/1994 | Brimhall | 604/165.03 |
| 5,685,859 | A | * | 11/1997 | Kornerup | 604/180 |
| 5,693,032 | A | * | 12/1997 | Bierman | 604/180 |
| 5,833,667 | A | * | 11/1998 | Bierman | 604/180 |
| 6,387,076 | B1 | * | 5/2002 | Landuyt | 604/174 |
| 6,428,516 | B1 | * | 8/2002 | Bierman | 604/174 |
| 6,447,485 | B2 | * | 9/2002 | Bierman | 604/174 |
| 6,491,664 | B2 | * | 12/2002 | Bierman | 604/180 |
| 6,572,588 | B1 | * | 6/2003 | Bierman et al. | 604/180 |
| 6,682,506 | B1 |  | 1/2004 | Navarro | |

(Continued)

FOREIGN PATENT DOCUMENTS

EP        286 525        10/1988

(Continued)

*Primary Examiner*—Kevin C Sirmons
*Assistant Examiner*—Emily Schmidt
(74) *Attorney, Agent, or Firm*—Leydig, Voit & Mayer, Ltd.

(57) ABSTRACT

A device for fixing a catheter, such as a peripheral veinous catheter, a central veinous catheter or a central arterial catheter, to the body of a patient. The device includes a housing, which can be closed by a lid, and a base coupled to the housing, surrounding the housing and enabling the housing to be fixed to the skin of the patient. The housing includes a first chamber through which the outer part of the catheter, which is placed in the vein, passes and a second chamber for accommodating and maintaining the catheter.

15 Claims, 7 Drawing Sheets

U.S. PATENT DOCUMENTS

| | | | |
|---|---|---|---|
| 6,770,055 B2 * | 8/2004 | Bierman et al. | 604/174 |
| 7,153,291 B2 * | 12/2006 | Bierman | 604/174 |
| 2004/0044306 A1 * | 3/2004 | Lynch et al. | 604/93.01 |
| 2004/0167475 A1 * | 8/2004 | Wright et al. | 604/180 |

FOREIGN PATENT DOCUMENTS

| | | |
|---|---|---|
| EP | 931 560 | 7/1999 |
| FR | 2 787 336 | 6/2000 |
| WO | WO 00/37136 | * 12/1998 |

* cited by examiner

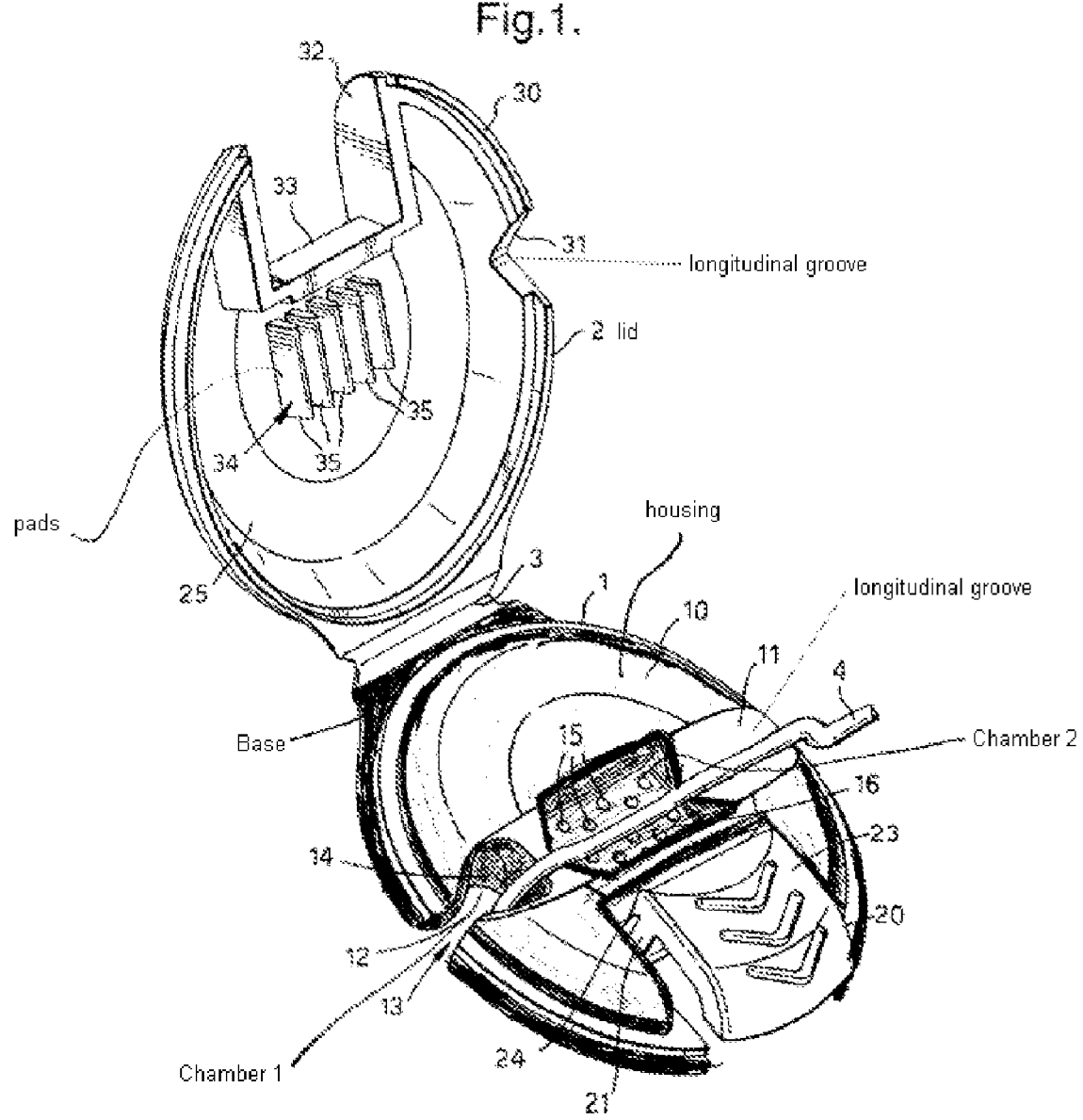

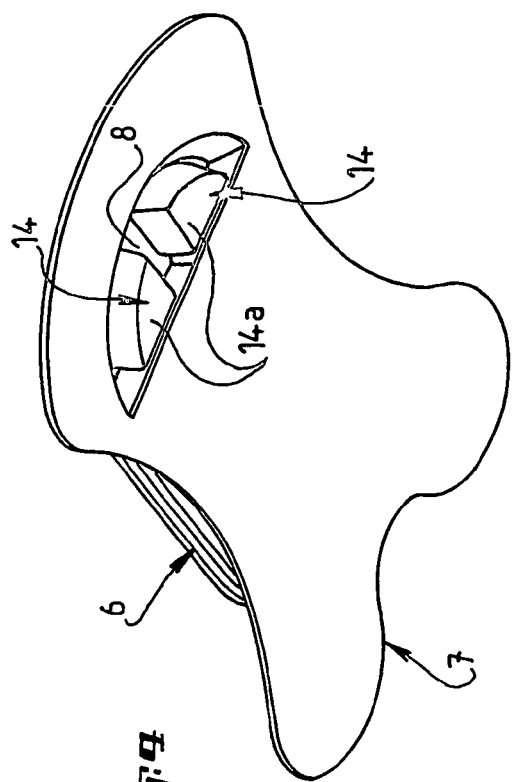
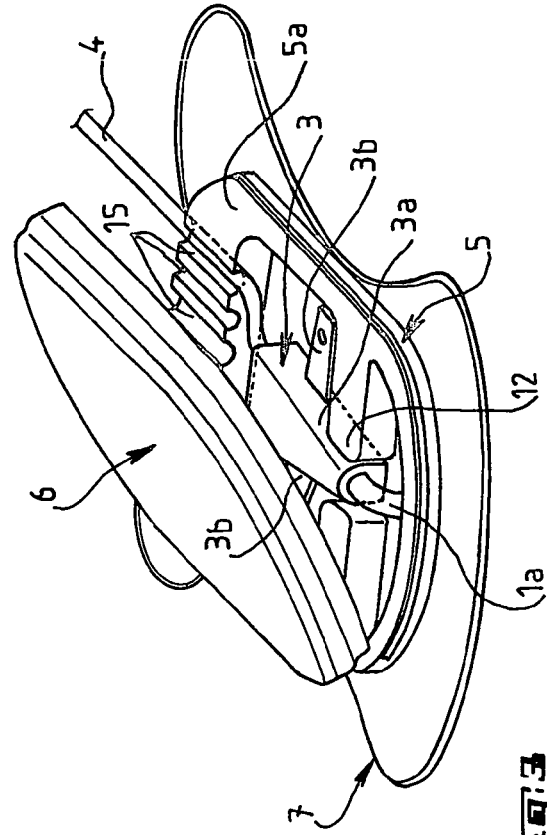
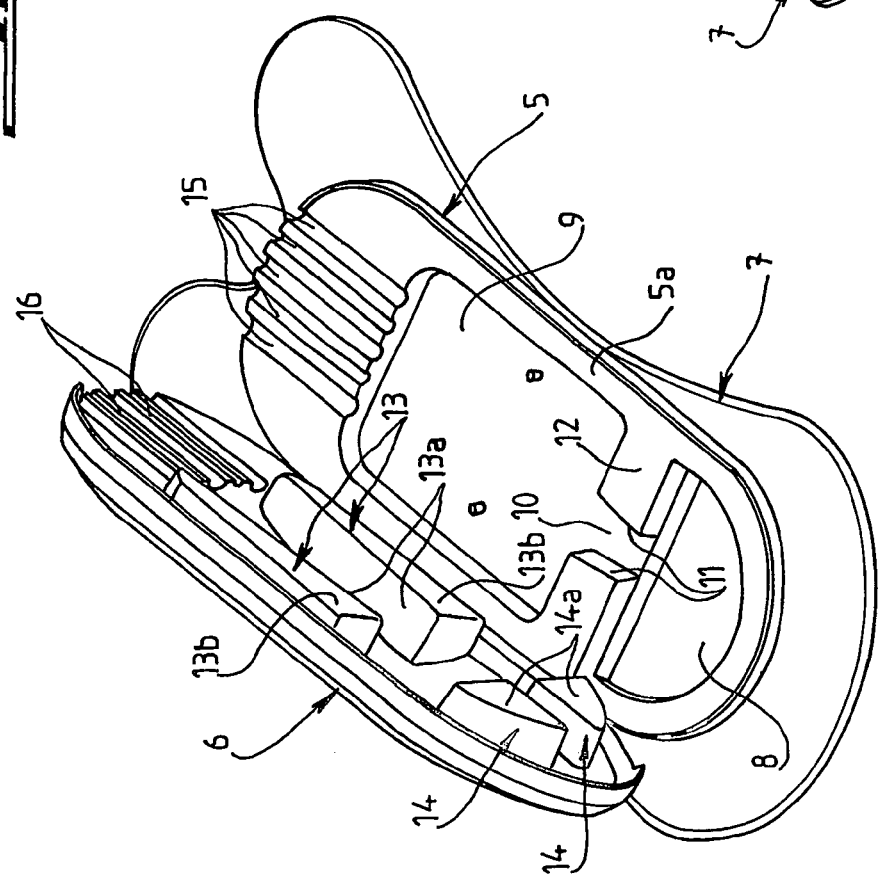

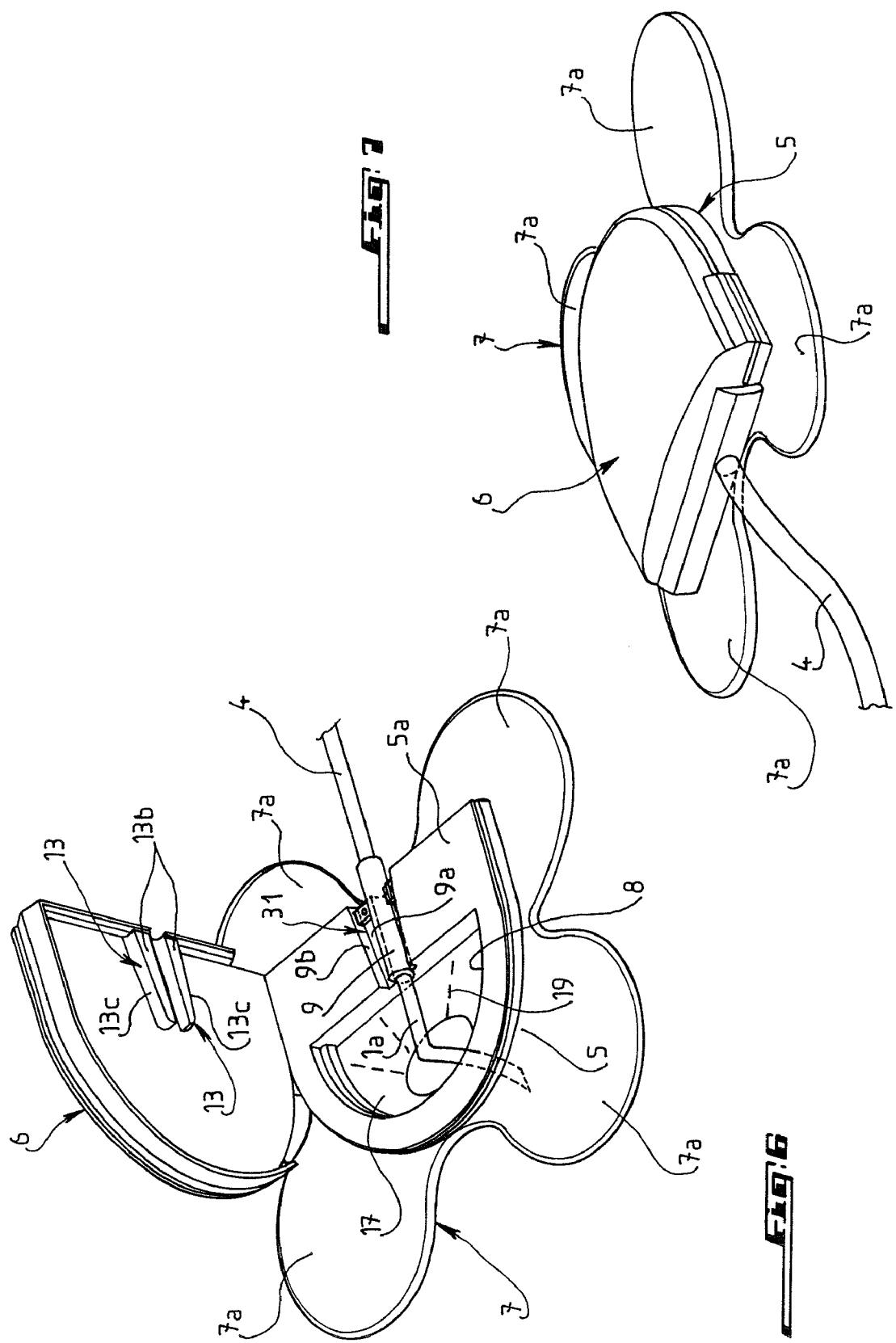

DEVICE FOR FIXING A CATHETER TO THE BODY OF A PATIENT

FIELD OF THE INVENTION

The present invention relates to a device for fixing a catheter to the body of a patient, for example, a peripheral venous catheter, a central venous catheter or a central arterial catheter, or a puncture needle, such as a Huber needle bent at a right angle.

BACKGROUND

The administration of medicinal products into the circulatory system of the human body is carried out either by the venous route or by the arterial route.

To administer these medicinal products, a catheter has to be placed, which consists of a tube having a smaller diameter than that of the venous or arterial vessels. Such catheters can be useful not only for the injection of medicinal products, but also to sense blood pressures in the venous system or in the arterial system.

In general, one distinguishes between two types of catheters: catheters for the peripheral venous routes and catheters for the central venous or arterial routes.

The peripheral venous catheters are placed at the level of a peripheral vein, that is, usually, at the level of the upper limbs of the patient, where the vein in question can be a vein of the forearm or a vein of the bend of the elbow. Among these catheters, there is the relatively short single venous catheter, having a length of approximately 5-6 cm, which is placed in a peripheral vein and whose part exiting from the vein is fixed to the skin of the patient using simple adhesives, to administer products or solutions over several hours, that is, over a relatively limited time period. The site of the puncture can be changed repeatedly as a function of the resistance of the peripheral veins.

The central venous catheter or the central arterial catheter is placed into deep venous trunks, that is into the large veins. Usually this means the internal or external jugular vein, the subclavian vein or the femoral vein.

The placement of these catheters is carried out by the cutaneous route, that is into the skin and in the location of the vein in which one wishes to place the catheter. For this, a cutaneous puncture is made into the vein through the intermediary of a rigid trocar, which is a kind of guide, fitted with a syringe at the end opposite the part which is introduced into the vein, allowing aspiration of the venous blood. Once this trocar is positioned in the venous trunk, the catheter is introduced after withdrawal of the syringe to allow the placement of this catheter in the vein of larger diameter.

As far as the central venous catheter or the central arterial catheter is concerned, it is connected at the end opposite the part which is introduced into the large vein, that is, immediately at the place where it comes out of the skin, to a support, generally a rigid plastic material, which constitutes a connection part which links this catheter to one or more catheters or external tubes, whose number can range up to five, and in which several different products circulate, which can be administered simultaneously, and which arrive in the support, which is in the form of a housing, and are then introduced into the catheter placed in the large vein. Usually, this support has a general triangular, sometimes circular, shape, and it is equipped with two external wings which allow the support to be fixed to the skin of the patient through the intermediary of a suture thread.

However, these different means of fixing catheters to the skin have the major drawback of being the sites of infections at the level of the puncture and penetration of the venous or arterial catheter, and, consequently, daily dressings have to be applied to prevent such infections, which may cause septicemia. In addition, when these dressings are placed at the femoral or jugular level, they create a real obstacle in the anatomical area, reducing the mobility and generating difficulties for the patient who wears a central venous catheter.

In addition, as already mentioned above, the catheters for the central venous routes have the drawback of using suture threads for fixing the support of this catheter, to which external catheters lead, with the associated risk for the operators, namely the intensive care personnel and the nurses.

Moreover, the administration of chemotherapy products is carried out using the central venous route, that is by placing a catheter in a large vein, and this catheter is connected to an injection chamber which is implanted under the skin generally at the level of the right or left pectoral muscle of the patient. Access is gained using the internal jugular artery, and the subcutaneous chamber is punctured using a Huber needle bent at a right angle and left in place as long as required for the chemotherapy product to be administered by perfusion under good conditions. The placement of this needle requires that it be maintained under the skin using adhesive means, which are not only unsuitable, but can sometimes result in infections at the sites of the cutaneous punctures as well. Consequently, dressings and compresses have to be used for protection to prevent any infection and allow the chemotherapy to be administered.

SUMMARY OF THE INVENTION

The purpose of the present invention is to eliminate the above drawbacks by providing a device which protects the area of the cutaneous puncture, which is often the site of infections, to control the puncture site and to prevent the use of daily dressings for cleaning the wounds.

For this purpose, in the invention a device for fixing to the body of a patient a catheter, such as a peripheral venous catheter, a central venous catheter or a central arterial catheter, or a puncture needle, such as a Huber needle bent at a right angle, comprises a housing which can be closed by a lid, a base integral with the housing and surrounding it and enabling the fixation of the housing to the skin of the patient. The housing comprises two chambers which communicate with each other, a first chamber which is located above the puncture site of the catheter or of the needle and traversed by the external part of the catheter which is placed in the vein or the artery, or by the needle which is implanted in the body of the patient, and a second chamber which allows the accommodation of a base of the catheter or of the needle. The base is retained in the second chamber and connected to at least one external tube, which is in fluid communication with the catheter or the needle through the base.

When the device is used for fixing a catheter, whose base constitutes a small reservoir of connection to the external tube, the housing is flat and it projects from its base along a relatively small height, and such that the first chamber and the second chamber are located approximately in the same plane and the lid comprises on its internal face two pads which penetrate into the chamber in the closed position of the lid so that they are applied, respectively, on the two lateral faces of the base of the catheter to maintain it bilaterally, relative to the flat bottom of the second chamber, which is also fixed to the skin of the patient.

The pads are applied, in the closed position of the lid, on two wings, respectively, which extend on either side of the lateral faces of the base of the catheter, to hold the latter against the bottom of the second chamber.

The two chambers are separated from each other by a wall, whose upper face is located in the plane of the upper face of the housing, and which comprises a communication passage defined by two oblique lateral faces which are perpendicular to the bottom of the second chamber and converge towards the first chamber, and such that the base of the catheter has lateral faces extending those which are retained by the pads, having a shape which matches the lateral faces of the passage to allow the base of the catheter to partially engage in the passage and to be retained therein.

The first chamber has a bottom which consists of a relatively thin flexible membrane which is fixed to the skin of the patient and comprises an opening allowing the passage of the base of the catheter and of the catheter.

The membrane comprises slits starting from the edge that delimits the orifice of the above-mentioned passage.

According to another embodiment, the lid comprises on its internal face two other pads which penetrate into the first chamber, in the closed position of the lid, so that they are arranged on either side of the external part of the catheter which is placed in the vein, closing off a large part of this chamber, and applied against the skin of the patient.

Each pad comprises on its face which is in contact with the skin a colloid which can contain antiseptic or antimicrobial substances.

The housing comprises on its upper face which delimits the second chamber, opposite the communication between the two chambers, at least one longitudinal groove for receiving the external tube, which is connected to the base of connection with a catheter, and the internal face of the lid also comprises at least one longitudinal groove which is located above the groove of the housing in the closed position of the lid, to maintain the tube with respect to the housing, where the tube which exits from this housing can be connected to blood perfusion, transfusion or collection means.

For the fixation of a central arterial catheter, the second chamber opens directly into the first chamber and it consists of a hollow part whose shape works in cooperation with an identical hollow part, which is defined between the two pads of the lid so as to form, in the closed position of the lid, a recess which matches the base of the central arterial catheter, making it possible to retain this base in the housing.

The fixation base of the housing consists of a sheet made of flexible material molding with the housing and, if applicable, the membrane of the first chamber, the faces of the bottom of the second chamber and of the membrane applied on the skin of the patient being continuous with the application face of the base on the skin.

The fixation base of the housing comprises at least two support holdfasts, each in the form of an ear.

The base comprises four support holdfasts in the form of ears.

The lid is mounted with articulation to the housing and it can be latched to the latter by a click mechanism.

The base of the housing is fixed to the skin of the patient by a colloid which can contain antiseptic or antimicrobial substances.

According to another embodiment, for the fixation of a Huber needle bent at a right angle, the second chamber is made through a wall of the housing and it opens directly into the upper part of the first chamber, where the chamber presents a transverse cross section in the shape of a U whose lateral walls diverge from the first chamber to accommodate the truncated base whose shape matches the second chamber of the needle, and the base of the needle is retained in the second chamber by at least two opposing catches that are integral with the lateral walls of the upper part of the second chamber at the upper part of the walls by being flush with the flat upper face of the housing, where the catches are elastically deformable towards the bottom of the second chamber to allow the base of the needle to be pushed into the chamber by embedding the base through the catches which rest on the base to retain it in the second chamber.

The device comprises two elastically deformable catches which are arranged at the upper part of the corresponding lateral wall of the second chamber by being spaced along this wall, where two opposite catches are transversely spaced with respect to each other.

A groove is provided in the second chamber between two spaced pairs of catches and it is intended to receive the part of the pad connecting an external tube to the truncated end of the base of the Huber needle in its assembly position in the housing.

The housing has the general shape of a bell whose wall, from which the second chamber opens to the outside, comprises at its lower part a notch which disengages the corresponding base part of the housing to confer a certain degree of flexibility to this base part.

The wall of the housing opposite the one which comprises the notch also comprises at its lower part a notch which disengages the corresponding part of the base of the housing to confer a certain degree of flexibility to this base part.

The housing is fixed to the body of the patient so that the first chamber is located vertically with respect to a chamber which is implanted under the skin, and the fixation of the base of the Huber needle in the second chamber allows the implantation of the free end of the Huber needle in the implanted chamber to administer products, notably chemotherapy products.

BRIEF DESCRIPTION OF DRAWING FIGURES

The invention will be understood better, and other purposes, characteristics, details and advantages of the invention will become clearer in the explanatory description below, which is made with reference to the schematic drawings, which are given only as examples illustrating several embodiments of the invention, and in which:

FIG. 1 is a perspective view of the device for fixing a catheter according to a first embodiment of the invention to the body of a patient;

FIG. 2 is a perspective view from a different angle of the device of FIG. 1, without the catheter;

FIG. 3 is a perspective view of the device of FIG. 1 in a semi-closed position of the lid of the housing of this device;

FIG. 4 is a top view of the device of FIGS. 1-3;

FIG. 6 is a perspective view of a third embodiment of the device of the invention;

FIG. 7 is a perspective view of the device of FIG. 6 whose housing is closed by its lid;

DETAILED DESCRIPTION

Figure 5:
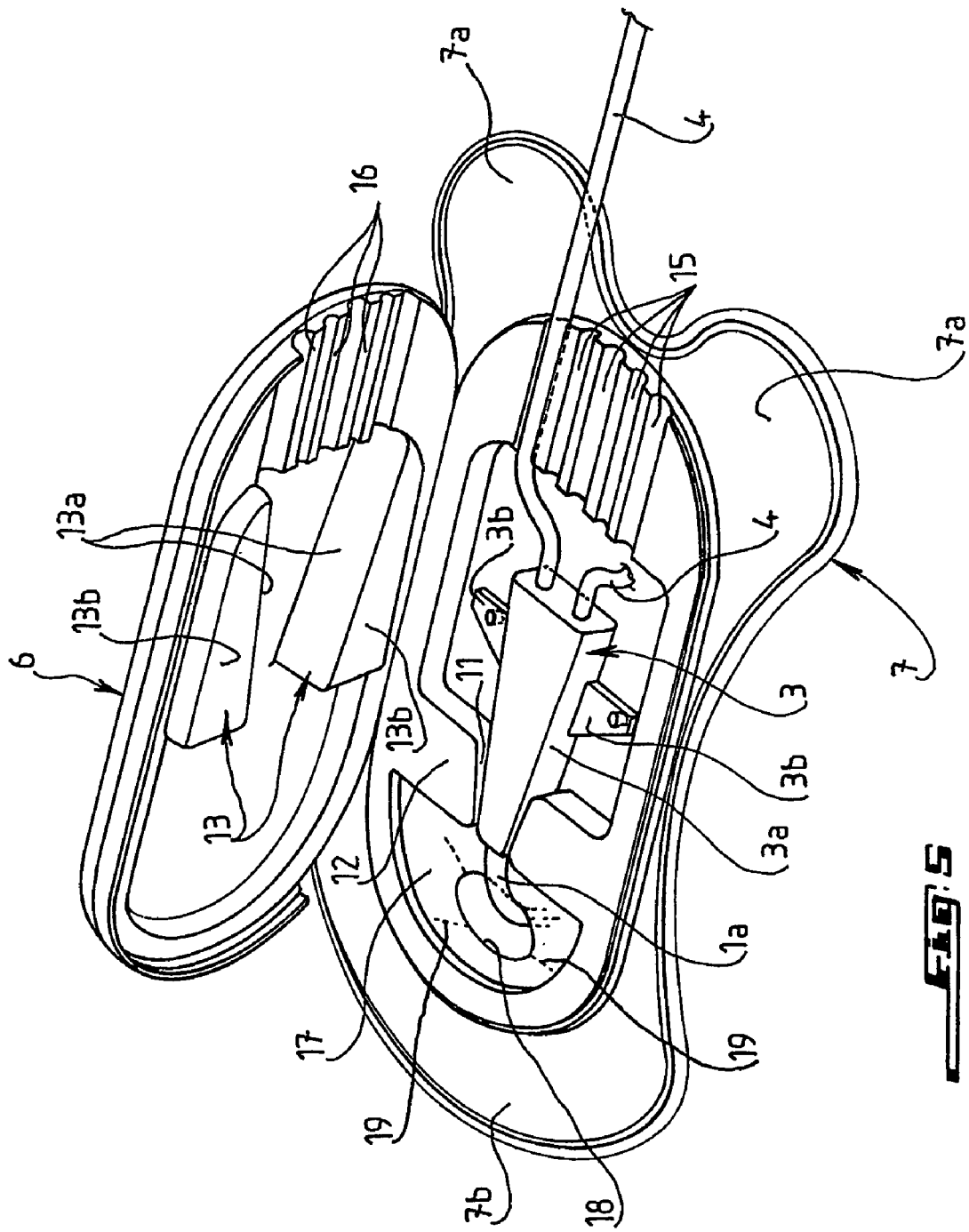
FIG. 5 represents a second embodiment of the fixation device of the invention.

The device which is represented in FIGS. 1-4 applies to the fixation to the body of a patient of a central venous catheter 1, which has been placed in a large vein 2 of the body of the patient by the subcutaneous route, where the external part 1a of catheter 1 exits from the skin P, and is attached to a support base constituting a small closed and sealed reservoir 3, which is connected at its end opposite the catheter 1 to at least one catheter or external tube 4 which is in fluid communication with the catheter 1 for the administration of a medicinal product in reservoir 3. One to five external catheters 4 can be connected to reservoir 3 to administer several different medicinal products in the vein 2 through the reservoir 3 and the venous catheter 1. Naturally, each external catheter 4 is connected to known perfusion means.

According to the invention, the device comprises a housing 5, which can be closed by a lid 6, which is mounted by articulation on a side of the housing which is flat and consequently has a relatively small thickness, for example, approximately 8-10 mm.

In addition, the device comprises a base 7 which is integral with the housing 5 by enclosing the latter to allow the fixation of the housing to the skin P of the patient, notably by a colloid.

The housing 5 comprises two chambers which are in communication with each other: a first chamber 8 traversing the bottom of the housing is located above the puncture site of the catheter 1 and traversed by the external part of this catheter, and a second chamber 9 in which the reservoir 3 for connection between the external catheter 4 and the venous catheter 1 is located.

As can be seen in FIG. 2, the chamber 8 can present a semicircular shape in a top view, while the chamber 9 can present a rectangular shape in a top view.

Given the relatively small thickness of the housing 5, the two chambers 8 and 9 are approximately in the same plane and they communicate with each other through the intermediary of a passage 10 which is delimited by two lateral walls 11, which are integral parts of the bottom of the chamber 9 perpendicularly with respect to the latter and inclined with respect to each other and converging towards the chamber 8. The passage 10 is provided through a wall 12 which is an integral part of the bottom part of the chamber 9 which is adjacent to the chamber 8 and whose flat upper face is part of the flat upper part 5a of the housing 5.

The reservoir 3 has a prismatic shape with a substantially rectangular transverse cross section, and its lateral walls 3a, which are arranged perpendicularly to the bottom of the chamber 9 when the reservoir 3 is housed in the latter chamber, are inclined with respect to each other and converge with each other towards the wall at the end of the connection of the reservoir 3 at the external part 1a of the catheter 1.

The reservoir 3 can comprise two wings 3b, which are an integral part of the lateral walls 3a symmetrically with respect to the longitudinal plane of the reservoir 3.

When the reservoir 3 is accommodated in the chamber 9 of the housing 5, the narrowest part of this reservoir, which forms a nose, is accommodated in the passage 10 with the corresponding parts of the oblique lateral walls 3a applied on the two lateral walls 11 of this passage, respectively. In this manner, the reservoir 3 is maintained in the passage 10 and it cannot move towards the chamber 8.

The lid 6 comprises two slender prismatic pads 13, which are integral parts of its face and arranged symmetrically with respect to the longitudinal median plane of the lid 6, and whose lateral opposite faces 13a, which extend perpendicularly to the internal face of the lid 6, are arranged obliquely with respect to each other in the same manner as the lateral walls 3a of the reservoir 3. With lid 6 closed, the two pads 13 penetrate into the chamber 9 and they are substantially applied by their oblique faces 13a, respectively, against the oblique walls 3a of the reservoir 3 to hold the latter bilaterally with respect to the housing 5. In addition, the pads 13 are applied by their terminal flat faces 13b respectively on the two wings 3b of the reservoir 3. In this manner, the reservoir 3, with lid 6 closed, is perfectly immobilized in the chamber 9, which prevents any accidental retraction of this reservoir and consequently of the venous catheter 1, thus eliminating any risk of severe hemorrhage. The wings 3b can be positioned at the bottom of the chamber 9 by two pins 9a which are integral parts of this bottom and engage in two perforations of the wings 3b.

The lid 6 comprises two other pads 14 which are integral parts of its internal face and penetrate into the chamber 8, with lid 6 closed, to partially close the latter. The two pads 14 are spaced with respect to each other so that they substantially extend the passage 10, with lid 6 closed, and are arranged on either side of the external part 1a of the venous catheter 1. In addition, the terminal flat faces 14a of the pads 14 are applied to the skin, with lid 6 closed, and, preferably, these terminal faces 14a can comprise a colloid or be used as a support for an antiseptic or antimicrobial product. Naturally, the external peripheral walls of the pads 14 have a shape which matches the peripheral walls which delimit the chamber 8 so that they are practically flush with the latter with lid 6 closed.

The housing 5 comprises, on its upper face 5a, opposite the wall 12, several longitudinal grooves 15, in the present case five, where each one has a semicircular transverse cross section and can receive an external catheter 4. The lid 6 also comprises identical longitudinal grooves 16, which are provided in its internal face and arrive above the longitudinal grooves 15, respectively, of the housing 5 with the lid 6 closed, to maintain between themselves the different external catheters 4, respectively, which are connected to the reservoir 3.

The lid 6 can be latched closed on the housing 5 by a ratchet mechanism, not shown, which can consist of a semicylindrical part of the free longitudinal edge of the lid 6, opposite its articulation, and a paired groove on the upper external edge of the housing 5, which receives the semicylindrical part.

The base 7 for fixing the housing 5 consists of a seat of flexible material which is an integral part, for example, by molding, of the housing 5 so that the lower application face of this assembly on the skin of the patient is flat and full, except at the place where the chamber 8 opens, and so that it can match the anatomical shape of the patient to which the device is to be fixed.

The lid 6 can be made of a single part by molding and, like the housing 5 and the base 7, it can be made of a plastic material.

According to this first embodiment, the base 7 is shaped, in a top view, so that it comprises two support holdfasts 7a, each in the shape of an ear, which are located opposite the chamber 8 and an opposite bent part 7b, which is adjacent to the chamber 8. The lid 6, and consequently the housing 5, presents, in a top view, a rectangular shape with bent ends.

The placement of the above-described device is carried out as follows. After the catheter 1 has been placed in the large vein, the reservoir 3 and the external part 1a of the catheter 1 are introduced through the chamber 8 of the housing 5, and the reservoir 3 is embedded in the passage 10 with application against the bottom of the chamber 9. Then, the external catheter(s) 4 is (are) connected to the reservoir 3 and arranged in their respective grooves 15, unless they are already connected to the latter when delivered, in which case the catheter(s) 4 is (are) first introduced through the window 8 before being arranged in their respective grooves 15 of the housing 5. Then, the operator folds back the lid 6 to bring it into its closed position, in which the pads 13 completely immobilize the reservoir 3 in the chamber 9 and the external catheters 4 relative to the housing 5, and the base 7, which is covered on its internal face with colloid, is fixed to the skin of the patient. The colloid which is applied to the internal face of the base 7 can be protected by an appropriate film, not shown, which is withdrawn before the device is applied to the skin of the patient. The colloid can contain antiseptic substances to achieve a considerable reduction of the risk of infection.

To visualize the puncture area of the catheter 1, the cap 6 can be made of a transparent plastic material.

The above-described device thus prevents any accidental extraction of the reservoir 3 from the venous catheter 1 and it can be adapted perfectly to the anatomical area of the patient, which makes the patient more comfortable and allows him/her to get about more easily. The device avoids the use of any fixation by means of sutures from the support or of the base in the form of a reservoir 3 to the skin.

The second embodiment of the device of the invention, which is represented in FIG. 5, differs from the device of the first embodiment only in the absence of the two pads 14 and the presence of a relatively thin flexible membrane 17 constituting the bottom of the chamber 8 and comprising an orifice 18, which allows the passage of the reservoir 3 with its wings 3b and of the external part 1a of the venous catheter 1 after the latter has been placed. The membrane 17 can comprise slits 19 which start from the edge of the orifice 18 to allow the passage of the reservoir 3 and of its wings through the orifice 18 by elastic deformation of the tongues defined between the different slits 19 extending radially in the case of a circular orifice 18. In addition, the internal face of the membrane 17, which is located in the same plane as the internal face of the base 7 and which can be prepared by molding to the latter, and the housing 5 can be coated with a colloid which makes it possible to apply the membrane 17 to the skin of the patient, and the colloid can comprise antiseptic or antimicrobial substances.

According to the third embodiment of FIGS. 6 and 7, the housing 5 is flat, as in the preceding embodiments, and in a top view it is in the shape of a semicircle which is extended by two parallel sides which are connected by a transverse side which defines the back wall of the housing 5 opposite the bent front wall, and the second chamber 9, which opens directly into the chamber 8, is defined by a slender hollow part with a semicircular transverse cross section, formed in the upper wall 5a of the housing 5 by extending perpendicularly to the right lateral wall of the chamber 8, of semicircular shape when seen from above. The hollow part 9 can taper from the end which opens into the chamber 8 to receive the sleeve-shaped catheter base 31 of the catheter 1, in the present case of the peripheral or arterial venous type with single channel, that is a single external catheter is connected to the catheter base 31. The latter can have a general truncated tapered shape paired to the reception chamber 9. The two pads 13 of the internal face of the lid 6 define, between themselves, a space whose shape matches the upper part of the catheter sleeve 9 to maintain the sleeve shaped catheter base 31 in the housing 5 with lid 6 closed. The recess which defines the chamber 9 is delimited at the upper part by two lateral flat faces 9a which are parallel to the upper face 5a of the housing 5 and connected to the latter by two flanges 9b extending obliquely by diverging opposite the chamber 8 in the case where the sleeve-shaped catheter base 31 is truncated. With lid 6 closed, the two pads 13 are simply applied with their end faces 13b and their external lateral faces 13c on the faces 9a and the flanges 9b, respectively.

The base 7 for fixation of the housing 5 is defined by four ear-shaped parts 7a, which are arranged symmetrically with respect to the longitudinal median plane of the device. The latter can comprise a flexible membrane 17, which constitutes the bottom of the chamber 8, as in the second embodiment.

The device of the fourth embodiment of the invention, which is represented in FIGS. 8-14, is particularly well suited to ensure the maintenance of a Huber needle bent at a right angle, allowing access to a catheter which is introduced, for example, into a jugular vein, and connected to a subcutaneously-implanted perfusion chamber.

The housing 5 of this device has lateral walls whose height is greater than the height of the housing 5 of each preceding embodiment, to take into account the vertical height of the needle 1 whose end must be introduced into the chamber which has been implanted under the skin. Thus, the housing 5 is fixed above the implanted chamber through the intermediary of its base 7, in such a manner that the chamber 8 is arranged vertically with respect to the implanted chamber to allow the introduction of the Huber needle into the latter chamber through the skin of the patient.

The reception chamber 9 of the sleeve 3 is provided through the corresponding lateral wall of the housing 5 in the upper part of the latter by opening into the chamber 8, at the upper part of the latter and partially at the upper face 5a of the housing 5. The chamber 9 presents a transverse cross section which is approximately in the shape of a U whose lateral walls taper from the chamber 8 to hold the matching truncated part of the sleeve of the catheter base 31, constituting the base of the Huber needle 1, which base forms a Luer female conical connection to which an external tube 4 can be connected.

The truncated chamber 9 for accommodating the sleeve-shaped catheter base 31 is delimited at the upper part of its lateral walls by two catches 9c, which are located on either side of a lateral wall, projecting from this wall and flush with the upper face 5a of the housing 5 towards the sleeve-shaped catheter base 31, in such a manner that they are arranged above the latter base in its position where it is mounted in the housing 5 to retain the sleeve-shaped catheter base 31 in the chamber 9. Each catch 9c of a lateral wall of the chamber 9 is located opposite catch 9c of the other lateral wall, thus defining a space between them which is transverse to the chamber 9, and two catches of a lateral wall are spaced longitudinally at this chamber 9. In addition, the catches 9c are elastically deformable towards the bottom of the chamber 9 to allow the embedding of the sleeve-shaped catheter base 31 in this chamber, as will be seen below. In the mounted position, the sleeve-shaped catheter base 31 has its truncated end part of larger diameter projecting from the housing 5, to which the external tube is connected, for example, through the intermediary of a male conical connection which is an integral part of this tube and engages in the sleeve-shaped catheter base 31. The sleeve-shaped catheter base 31 is thus retained not only by the catches 9c, but also by clamping in the truncated chamber 9, and the part of the Huber needle 1 which is curved at a right angle, and which is introduced into the chamber which has been implanted under the skin, extends approximately along the longitudinal or vertical axis of the chamber 8 whose general shape is cylindrical. An internal groove is formed in the chamber 9 between two longitudinally spaced pairs of catches 9c, and opens at the upper face 5a of the housing 5 between two adjacent catches. The role of the groove 9d will be explained later with reference to FIGS. 12 and 13.

Figure 8:
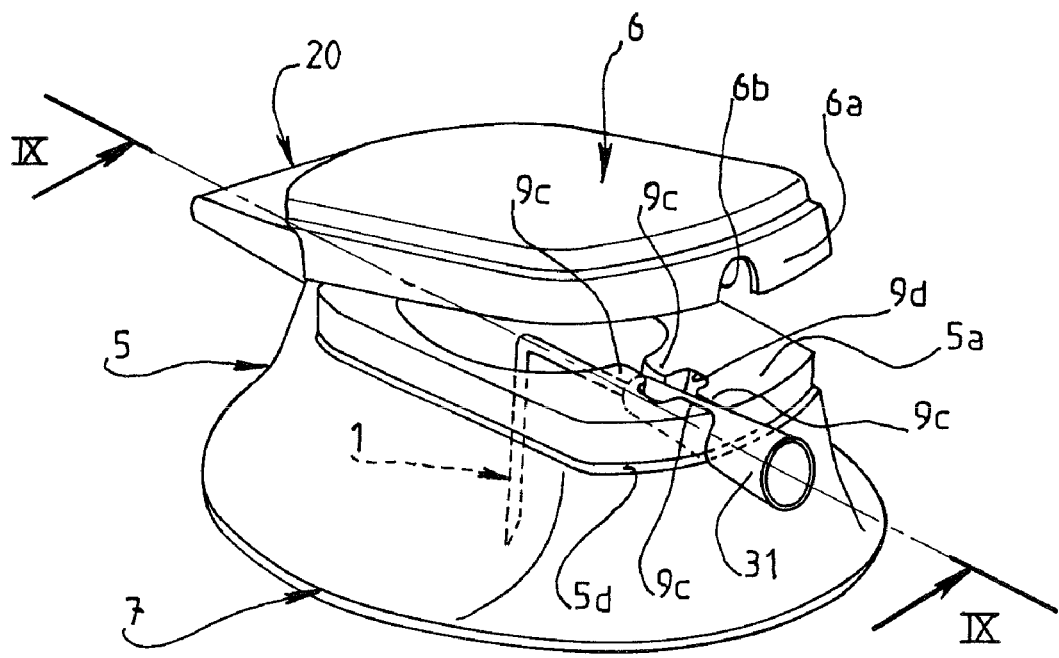
FIG. 8 is a perspective view of a fourth embodiment of the device of the invention.
Figure 9:
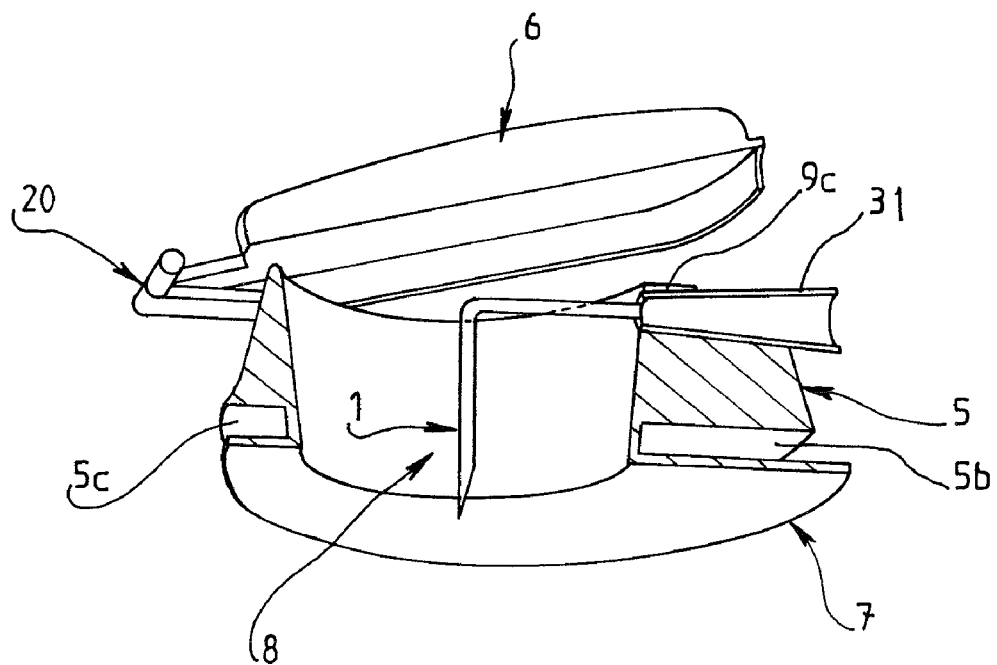
FIG. 9 is a cross-sectional view in the longitudinal median plane containing the line IX-IX of the device of FIG. 8.
Figure 10:
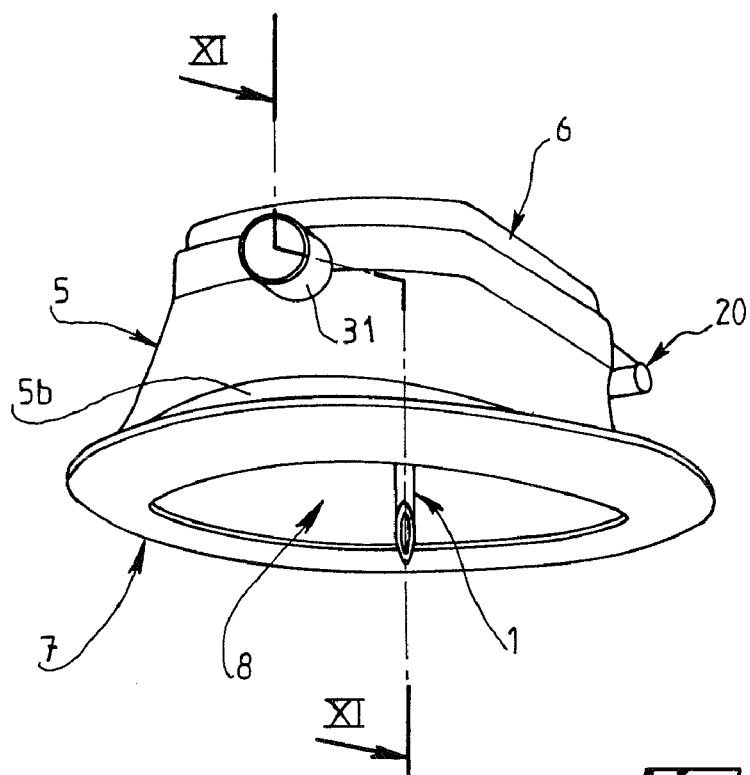
FIG. 10 is a perspective view from a different angle of the device of FIG. 8.
Figure 11:
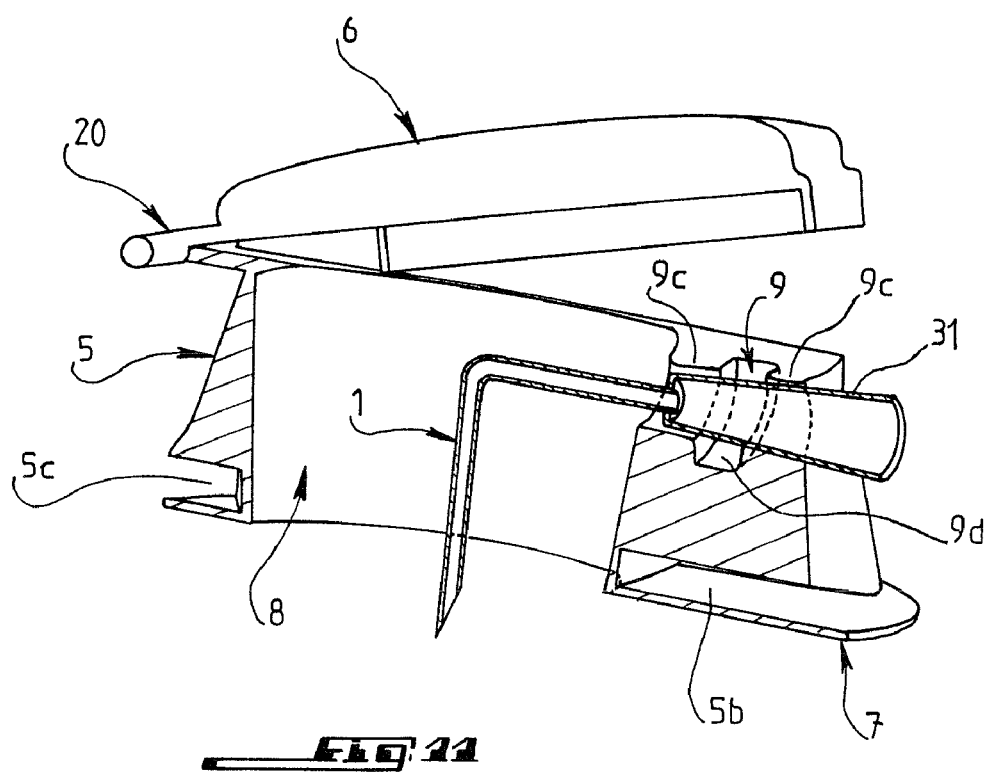
FIG. 11 is a cross-sectional view along the longitudinal median plane containing the line XI-XI of the device of FIG. 10.

As is more apparent in FIGS. 8 and 10, the housing 5, with its base 7, presents the general shape of a bell and it comprises, at the lower part of its wall into which the sleeve-shaped catheter base 31 projects, a hollow part or notch 5b, which is located above the base in the form of a sheet 7, thus releasing to a large part the base 7 of this wall, conferring to it a flexibility which allows it to be molded to the anatomical area of the patient to which the housing 5 is to be fixed. Similarly, the internal part of the wall of the housing 5, which is opposite the wall from which the sleeve-shaped catheter base 31 projects and located vertically with respect to the articulation hinge 20 of the lid 6 on the housing 5, comprises a hollow part or notch 5c which separates a large part of the base 7 from this wall to confer to it the flexibility required for the fixation of the housing 5 to the skin of the patient. The remaining parts of the base 7 are integral parts of the other lateral walls of the housing 5, connecting to the two above-mentioned transverse walls.

The lid 6 is latched to its position of closing the housing 5 by ratchet mechanisms which are known in themselves, and which can be located at the level of the lower edge of the front wall 6a of the lid 6 and of an edge 5d of the housing 5 on which rests the lower edge of the front wall 6a, which comprises a substantially semicircular cutout 6b, covering the sleeve-shaped catheter base 31 in the closed position of the lid.

As in the preceding embodiments, the housing 5 and the lid 6 can be made by molding a plastic material.

The placement of the device of FIGS. 8-11 is carried out by first fixing the housing 5 to the anatomical area of the patient by the base 7, whose internal face is provided with a colloid which comprises antimicrobial or antiseptic substances, the chamber 8 being arranged vertically with respect to the chamber which was implanted earlier under the skin of the patient. Then, the operator pushes the sleeve-shaped catheter base 31 of the needle 1 into the chamber 9 by embedding through elastically deformable catches 9c, until the sleeve-shaped catheter base 31 is applied on the bottom of the chamber 9, where it is retained by the catches 9c which rest on the sleeve-shaped catheter base 31. At the same time, the vertical part of the Huber needle 1 is automatically implanted by its lower end into the chamber which was implanted through the skin of the patient. After the chemotherapy products have been administered to the patient, the retraction of the needle 1 is carried out by pulling the needle 1 upward and its sleeve-shaped catheter base 31 against the elastic return force of the catches 9c.

Once the Huber needle 1 is implanted in the subcutaneous chamber, the operator folds the lid 6 to latch it to the housing 5.

This device thus eliminates any risk of accidental retraction of the Huber needle and considerably lowers the risk of infection.

Figure 12:
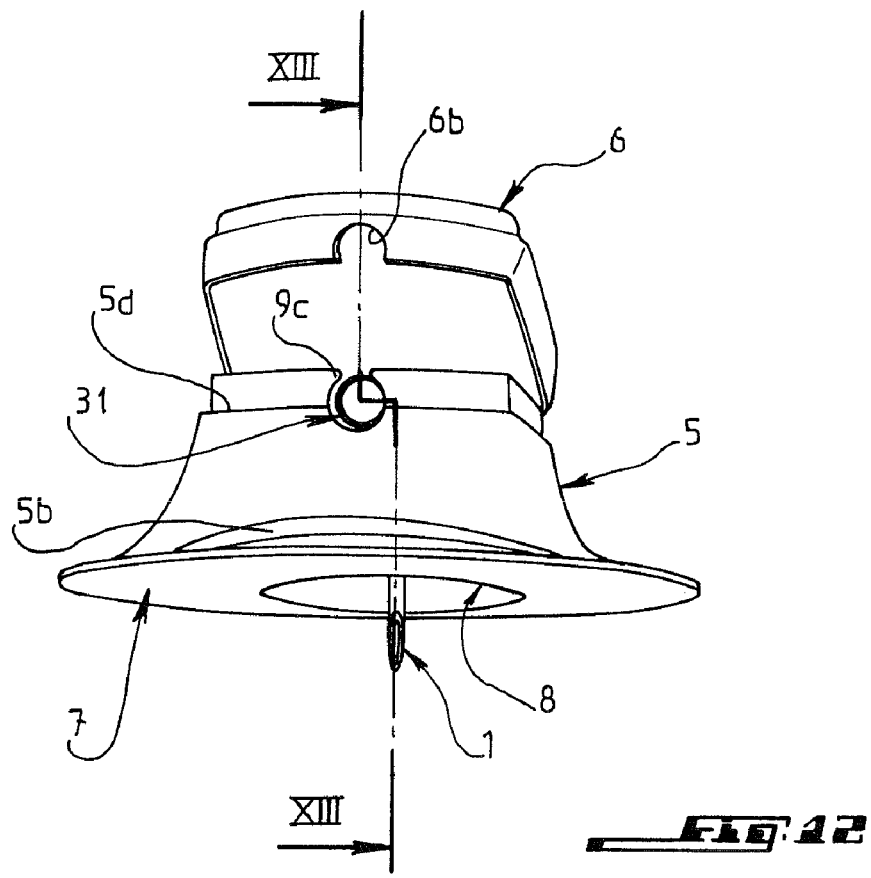
FIG. 12 is a perspective view representing another use of the device of FIG. 8.
Figure 13:
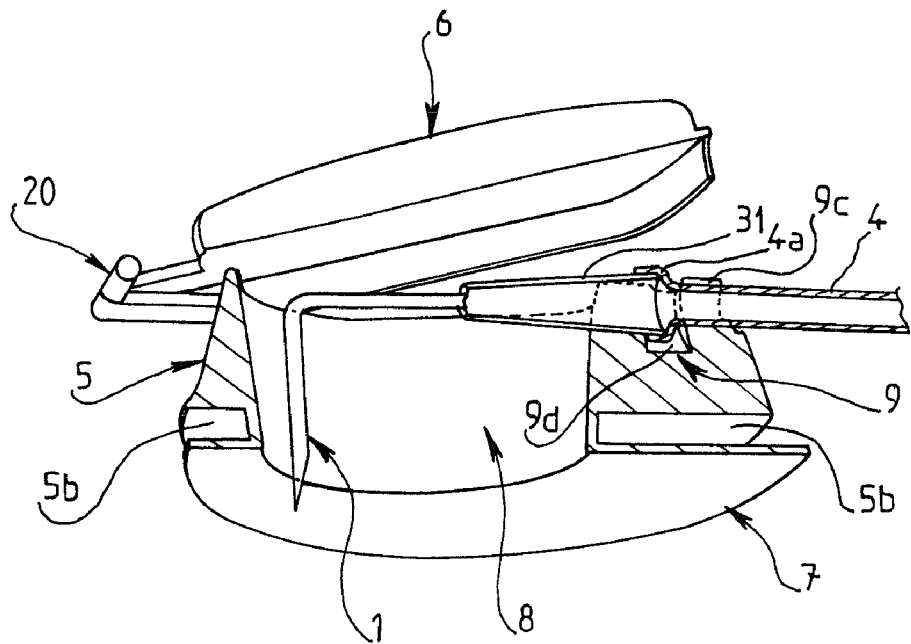
FIG. 13 is a partial cross-sectional view along the longitudinal median plane containing the line XIII-XIII of FIG. 12.

The device of FIGS. 8-11 can be used with a Huber needle 1 whose sleeve-shaped catheter base 31 is connected to the external tube 4 which is forced on the truncated free end of the sleeve-shaped catheter base 31, forming an external pad 4a as represented in FIGS. 12 and 13. In this case, the part of connection with pad 4a is embedded in the groove 9d so that the truncated end part of the sleeve-shaped catheter base 31 is held at the bottom of the chamber 9 with two of the catches 9c covering the upper face of the sleeve-shaped catheter base 31 and the connection tube is just covered by the two other catches 9c immediately before exiting from the housing 5. Thus, the end part of the sleeve-shaped catheter base 31 does not project from the housing 5, since it is accommodated in a part of the chamber 9 which opens towards the chamber 8, and the remaining part of the catheter base sleeve 31 projects into the chamber 8 with the vertical part of the Huber needle 1 being located in proximity to the corresponding lateral face of the chamber 8, as can be seen in FIG. 13. Naturally, the truncated end part of the catheter base sleeve 31 has dimensions such that it is received in the part which has the same shape as the opening from chamber 9 into chamber 8. As far as the rest is concerned, the placement and the retraction of the Huber needle is carried out in the same manner as in FIGS. 8-11.

In summary, the device of the invention which is the object of each one of the above-described embodiments effectively protects the cutaneous puncture area from infections, it allows examination of the puncture site and it eliminates the use of daily dressings for cleaning the wounds.

In addition, the flexibility of the fixation base of the device makes it possible to adapt it to the anatomical area of the patient where it is to be arranged, and it confers greater comfort to the patient, allowing him/her to get about and move more easily. In addition, the device avoids the use of fixation of the catheters to the skin by means of suture threads. The use of a colloid for fixing the base to the skin, which can contain antiseptic and antimicrobial substances, considerably decreases the risks of infection.

What is claimed is:

1. An assembly fixing a catheter to a patient, comprising:
   a catheter including a supporting base comprising a reservoir having a first end connected to a part of the catheter that is implanted in the patient and a second end connected to at least one external tube that is in fluid communication with the catheter through the reservoir, a fluid flow direction extending from the at least one external tube, through the reservoir, and to the part of the catheter implanted in the patient;
   a housing;
   a lid closing the housing; and
   a base integral to the housing and surrounding the housing, for fixation of the housing to skin of the patient, wherein
      the housing comprises first and second chambers which communicate with each other through a passage between the first and second chambers,
      the first chamber includes a bottom wall opening through which the part of the catheter that is implanted in the patient passes,
      the second chamber includes a bottom wall,
      the supporting base of the catheter that includes the reservoir is accommodated partially in the passage between the first and second chambers and partially in the second chamber,
      the first end of the reservoir is located at the first chamber in the passage and the second end of the reservoir is located in the second chamber,
      the supporting base of the catheter includes first and second wings respectively extending, transverse to the fluid flow direction, from opposite lateral faces of the supporting base,
      the lid includes, on an internal face, first and second pads generally parallel to the fluid flow direction and which, when the lid is closed, penetrate into the second chamber, respectively contact the first and second wings, and hold the supporting base of the catheter against the bottom wall of the second chamber, and the lid comprises, at the internal face, two external pads which, when the lid is closed, penetrate into the first chamber, are disposed on opposite sides of the part of the catheter that is implanted in the patient, substantially close the first chamber, and rest against the skin of the patient.

2. The assembly according to claim 1, wherein the housing is flat and has a relatively small height with respect to the base, the first chamber and the second chamber are approximately co-planar, and the first and second pads hold the supporting base of the catheter bilaterally with respect to the bottom wall of the second chamber.

3. The assembly according to claim 2, wherein
the passage through which the first and second chambers communicate is defined by two oblique lateral faces which are perpendicular to the bottom wall of the second chamber and converge towards the first chamber, and
the lateral faces of the supporting base of the catheter are complementary to the lateral faces of the passage so that the supporting base of the catheter partially engages the lateral faces of the passage and is retained in the passage.

4. The assembly according to claim 1, wherein the first chamber has a bottom wall comprising a relatively thin flexible membrane for fixing to the skin of the patient and the bottom wall opening comprises an orifice in the thin flexible membrane through which the catheter passes.

5. The assembly according to claim 4, wherein the membrane comprises slits extending from an edge which delimits the orifice.

6. The assembly according to claim 1, wherein each external pad includes, on a face for contacting the skin, a colloid.

7. The assembly according to claim 3, wherein
the housing comprises, on an upper face, which delimits the second chamber, opposite the communication passage, at least one longitudinal groove, and
the internal face of the lid comprises at least one longitudinal groove which is located opposite the groove of the housing, when the lid is closed, for holding the external tube relative to the housing.

8. The assembly according to claim 1, wherein the second chamber includes a hollow part having a shape cooperating with a hollow part defined between the first and second pads of the lid to form, when the lid is closed, a recess which matches the supporting base of the catheter, retaining the supporting base in the housing.

9. The assembly according to claim 4, wherein
the base for fixing the housing includes a sheet of flexible material which is molded with the housing and,
a face of the bottom wall of the second chamber and a face of the membrane are continuous with the base.

10. The assembly according to claim 9, wherein the base for fixing the housing comprises at least two support holdfasts, each holdfast having the shape of a human ear.

11. The assembly according to claim 10, wherein the base for fixing the housing comprises four support holdfasts in the shape of human ears.

12. The assembly according to claim 1, wherein the lid is articulated to the housing and latches to the housing.

13. The assembly according to claim 1, wherein the base includes a colloid for fixing the base to the skin of the patient.

14. The assembly according to claim 2, wherein the lateral faces of the supporting base are oblique to each other and the first and second pads have opposed lateral faces that are oblique to each other and, when the lid is closed, respective lateral faces of the first and second pads press against corresponding lateral faces of the supporting base.

15. The assembly according to claim 1 wherein the lid is transparent for observing the catheter when the lid is closed.

* * * * *